United States Patent [19]

Huber et al.

[11] Patent Number: 4,991,960
[45] Date of Patent: Feb. 12, 1991

[54] ATOMIC ABSORPTION SPECTROMETER

[76] Inventors: Bernhard Huber, Hildegardring 42, 7770 Überlingen; Rolf Tamm, Am Fohrenbuhl 8, 7777 Salem 2; Toma Tomoff, Lawendelweg 9, 7770 Überlingen; Gunther Dencks, Prielstrasse 3, 776 Owingen, all of Fed. Rep. of Germany

[21] Appl. No.: 893,766
[22] Filed: Aug. 6, 1986

[30] Foreign Application Priority Data

Aug. 7, 1985 [DE] Fed. Rep. of Germany ....... 3528300

[51] Int. Cl.$^5$ ..................... G01N 21/72; G01N 21/31
[52] U.S. Cl. .................................... 356/307; 356/315
[58] Field of Search .............. 356/315, 417, 434, 440, 356/307

[56] References Cited

U.S. PATENT DOCUMENTS

| | | | |
|---|---|---|---|
| 1,967,583 | 7/1934 | McFarlane et al. | 356/434 |
| 2,043,589 | 6/1936 | Huller | 356/434 |
| 4,291,986 | 9/1981 | Satou et al. | 356/440 X |
| 4,406,541 | 10/1983 | Tomoff et al. | 356/312 |
| 4,508,451 | 4/1985 | Stockdale | 356/315 |

FOREIGN PATENT DOCUMENTS 2950105 6/1981 Fed. Rep. of Germany .

OTHER PUBLICATIONS

"Mikrochim. Acta", Von Walter Lang, May 4, 1964, pp. 796–808, Flammenspektrophotometrische Absorptionsmessungen mit peridisch ausgelenkter Flamme.

Primary Examiner—Vincent P. McGraw
Attorney, Agent, or Firm—Thomas P. Murphy; Edwin T. Grimes

[57] ABSTRACT

In an atomic absorption spectrometer, a burner 16 for atomizing a sample is movable between a first and a second position. In the first position, the "cloud of atoms" is formed in the area of the housing-fixed measuring light beam 14. In the second position, it is formed outside the measuring light beam. The measurement is made in the first position whereby the utilization of the energy of the measuring light beam is optimal. A drift compensation is made in the second position to take care of variations of the lamp intensity and of the detector sensitivity.

18 Claims, 4 Drawing Sheets

ATOMIC ABSORPTION SPECTROMETER

BACKGROUND AND SUMMARY OF THE INVENTION

This invention relates to atomic absorption spectrophotometry and more particularly to an atomic absorption spectrometer and method for correcting for variations in the light source-detector assembly.

An atomic absorption spectrometer generally comprises a light source emitting a line spectrum with the resonant lines of a looked-for element and an optical system generating a measuring light beam originating from the light source and impinging upon a detector. An atomizing-means transforms the sample substance into an atomic state so that a "cloud of atoms" is generated in the path of the measuring light beam. The atomizer means may be a burner with the liquid sample being sprayed into the burner flame. The atoms of the looked-for elements absorb the measuring light beam whereas the measuring light beam is substantially unaffected by atoms of other elements. Therefore, the measuring light beam undergoes an attenuation which depends on the quantity of the looked-for element in the cloud of atoms and thus in the sample. Atomic absorption spectroscopy is a very sensitive and very accurate method for determination of concentrations of a looked-for element in a metered sample.

Essential for this measurement, however, is an exact knowledge of the zero line, i.e., the intensity of the measuring light beam measured in the absence of the looked-for element in the sample. This zero line can change by variation of the lamp intensity or the detector sensitivity and such variations would immediately affect the measurement.

Double beam spectrophotometers are known in which a light beam originating from a light source is alternatingly directed through a measuring path and a reference path by a chopper arrangement. The sample to be measured is arranged in the measuring path and a reference sample is arranged in the reference path. The beams subsequently are recombined by a semitransparent mirror or another chopper and impinge upon a common detector. The signal obtained with the reference path then forms the zero line to which the signal obtained with the measuring path can be referenced. The change between the measuring and reference path conventionally is effected with line frequency. Such double beam spectrophotometers suffer from the disadvantage that the measuring light beam impinges upon the detector only during, at most, half of the time. When the sample is a cloud of atoms in a flame, a relatively high noise level results. Therefore, efforts have to be made to utilize the energy of the desired signal as completely as possible in order to obtain a favorable signal-to-noise ratio. Accordingly, in a double beam apparatus, a periodic fast change between a measuring path of rays and a reference path would be disadvantageous and would reduce the sensitivity of the atomic absorption spectrometer.

In EP-A-84 391, an atomic absorption spectrometer is disclosed in which a reference path of rays is provided which avoids the flame. This reference path of rays provides at the detector a signal changing only with the apparatus drift caused by variation of the lamp intensity or by variation of the detector sensitivity. This signal serves for compensation of the drift in signals obtained by the measuring path of rays through the flame. For this purpose, movable mirrors are moved into the measuring path of rays between the sample measurements. The light is directed along the reference path and reflected by mirrors from the reference path again, to the entrance slit of a common monochromator.

During the measurement, the light beam passes from the light source only through the measuring path such that the total energy of the light beam is available for the measurement and a favorable signal-to-noise ratio results. The measurement through the reference path is made while the flame stabilizes after a sample change.

The pivoting of mirrors into the path of rays of the measuring light beam in order to direct the light beam into the reference path and subsequently reflecting it back into the measuring path requires high precision of the mirrors to be pivoted. Errors in the alignment of these mirrors enter into the direction of the reflected light beam with twice the angle. This, in turn, can affect the intensity of the light beam passing through the entrance slit of the monochromator.

Accordingly, it is an object of the present invention to provide a new and improved atomic absorption spectrometer.

Another object is to provide such a spectrometer which attains an enhanced signal-to-noise ratio while compensating for light source and detector variations.

Another object of the invention is to provide such a spectrometer which avoids movable mirrors and the associated precision alignment thereof.

A further object of the invention is to provide such a spectrometer having fixed stationary optical elements defining a single fixed optical path for both sample and reference measurements.

A still further object of the invention is to provide a spectrometer having a selectively movable atomizer for selective positioning of the atomized sample within and without a fixed optical path.

Another object of the invention is to provide a new and improved method of compensating for light source-detector variations in an atomic absorption spectrometer.

Accordingly, it has been found that the foregoing and related objects and advantageous are attained in an atomic absorption spectrometer having a housing, a line emitting light source, a detector for measuring the absorption of light from the light source, and optical means for generating a measuring beam along a fixed optical path from the light source to the detector with the optical path extending through the housing. An atomizer for atomizing a sample to generate a cloud of atoms for atomic absorption analysis with the light beam is movably mounted within the housing for movement between a first sample measurement position wherein the cloud of atoms from the atomizer is within the optical path and a second reference measurement position wherein the cloud of atoms is without the optical path. A microprocessor control controls a sample measurement when the atomizer is in the first position and a reference measurement when the atomizer is in the second position to compensate the sample measurement based upon the reference measurement. The atomizer is a flame burner atomizer mounted to a moldable support carriage for movement between the sample measurement position and the reference measurement position. An adjustable mounting assembly permits selective adjustment of the mounting of the burner with respect to level and angle.

In this arrangement, the measuring light beam remains the same both during the sample measurement as during the drift compensation. The measuring light beam selectively passes uninterruptedly through the "cloud of atoms" during the measuring time and a drift compensation is effected outside the measuring time. The measuring light beam is exclusively directed by stationary, optical elements of the imaging optical system which have been accurately adjusted once and forever, and movable mirrors and the associated precision requirements thereof are avoided. Instead, the atomizer burner is displaced into and out of the stationary measuring light beam. The displacement of the burner can be effectively and reliably accomplished with relatively low costs. The guiding of the burner does not require extreme precision since the position of the burner does not have an influence on the position of the measuring light beam and the burner can be reproducibly moved into the sample measurement position with simple means.

The method of light source-detector variation compensation of the present invention includes directing a light beam for atomic absorption spectrometry along a predetermined fixed optical path between a light emitting source and a detector assembly for performing sample and reference measurements. An atomizer is positioned in a first predetermined position so that the atomized sample therefrom is in the optical path of the light beam. A sample measurement is performed with the total available energy of the light beam with the atomizer in the first position. The atomizer is positioned in a second predetermined position so that the atomized sample is without the optical path and a reference measurement is performed. The sample measurement is corrected to compensate for light source variations based upon the reference measurement.

DESCRIPTION OF THE PREFERRED EMBODIMENT

Figure 1:
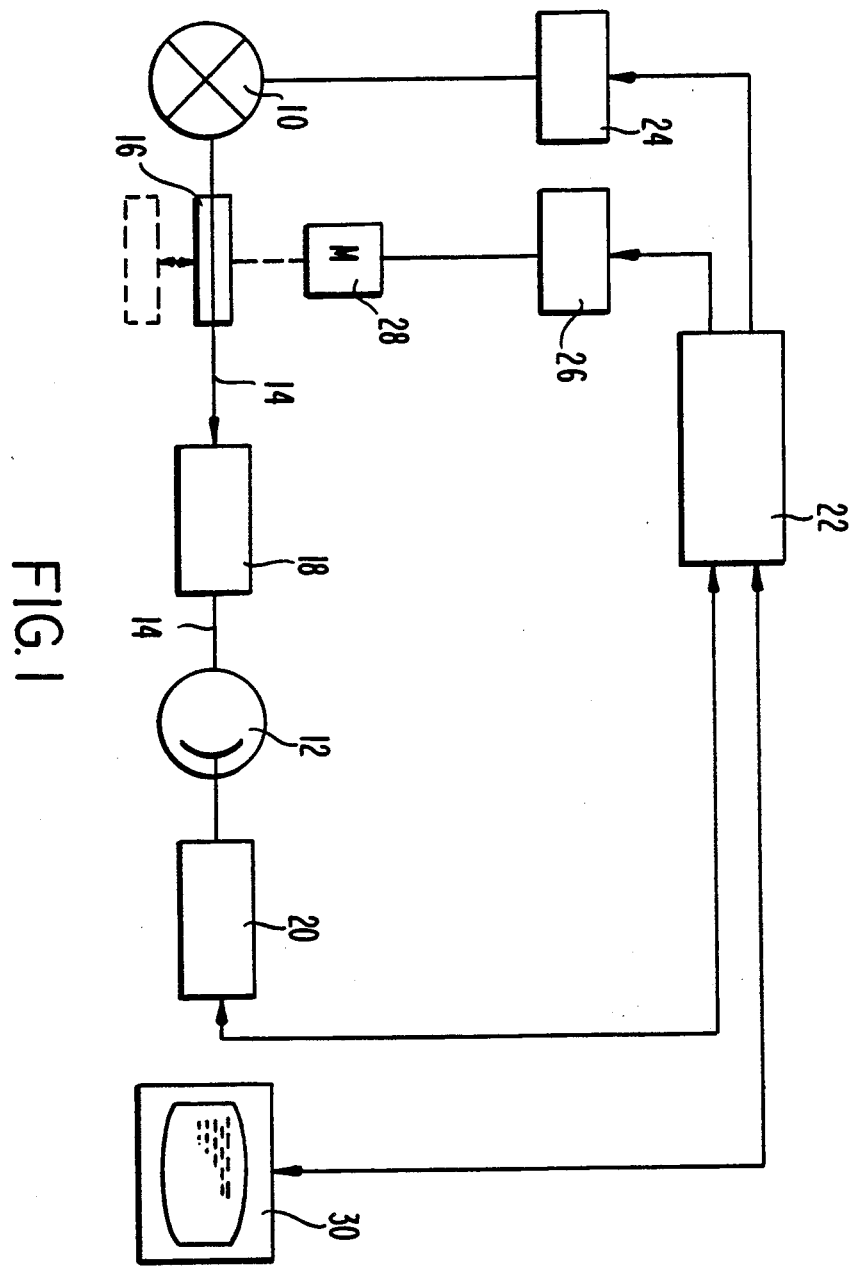
FIG. 1 is a block diagram of an atomic absorption spectrometer of the present invention with a movable atomizer burner.

Although specific forms of the present invention have been selected for illustration in the drawings, and the following description is drawn in specific terms for the purpose of describing these forms of the invention, the description is not intended to limit the scope of the invention which is defined in the appended claims.

Referring to FIG. 1, the atomic absorption spectrometer of the present invention is generally designated by the numeral 11 and includes line emitting light source 10 in the form of a hollow cathode lamp and a detector 12 for responding to the light of the light source 10. An optical system generates a measuring light beam 14 originating from the light source 10 impinging upon the detector 12. The measuring light beam 14 passes through atomizing means for atomizing a sample and generating a cloud of atoms. Herein the atomizing means is an atomic burner 16 disposed below the measuring light beam 14. The measuring light beam 14 passes through a monochromator 18 before it impinges upon the detector 12. The monochromator 18 selects a characteristic spectral line from the line spectrum emitted by the light source 10.

A signal processing circuit 20 is connected to the detector 12 and a microprocessor 22. The output signal of the detector 12 is inputted to the signal processing circuit 20. The microprocessor 22, on one hand, controls the signal processing circuit 20 and, on the other hand, receives signals for data processing from the signal processing circuit 20 for analysis measurement including variation compensation based upon reference measurements. The microprocessor 22 controls a current supply 24 for the light source 10 as well as a motor control 26. The motor control 26 controls a servomotor 28 by which the burner 16 is movable from the illustrated sample measurement position into the reference measurement position (shown in broken lines) outside the measuring light beam 14. The measuring values obtained are supplied by the microprocessor 22 to a display unit 30.

Figure 2:
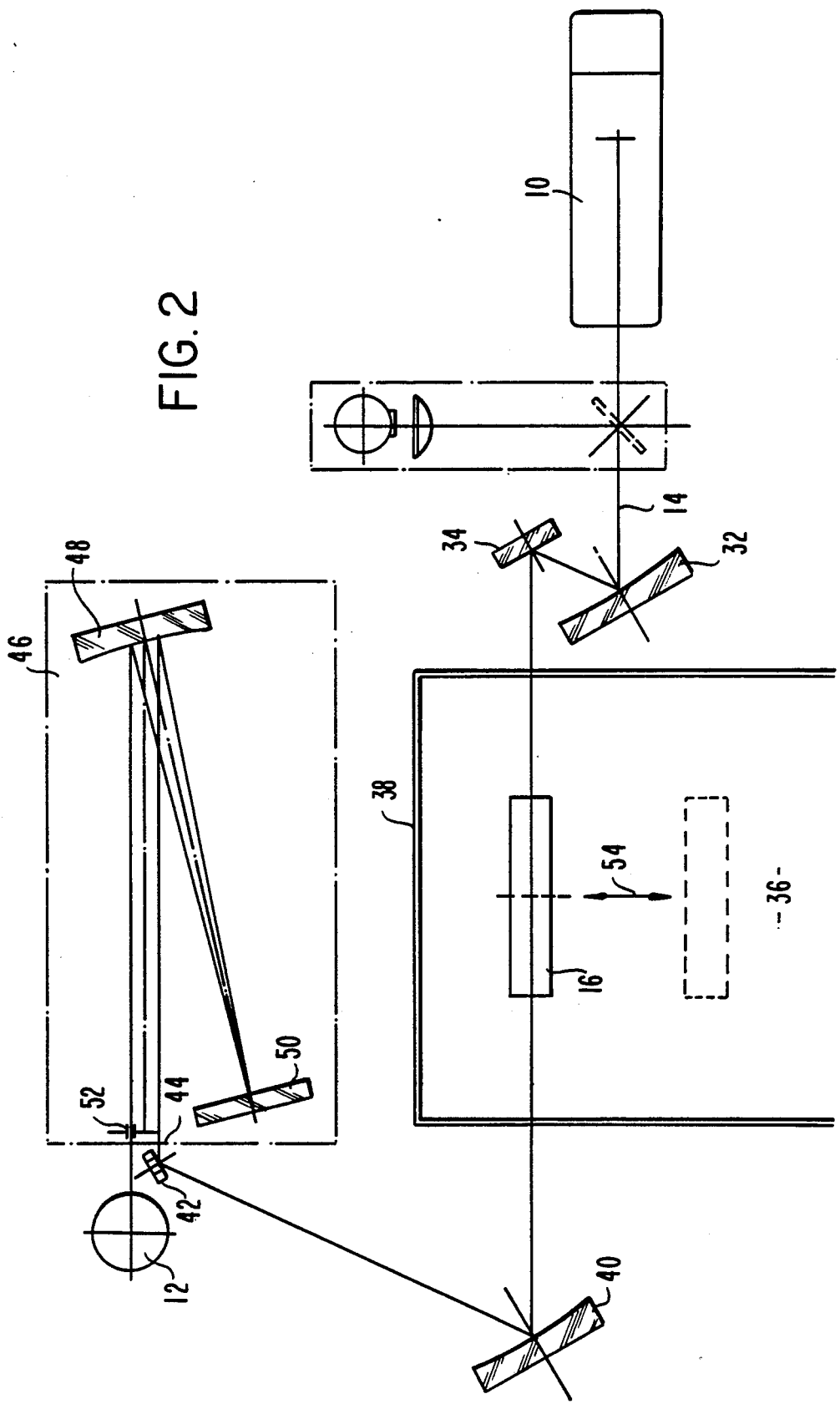
FIG. 2 is a schematic illustration of the path of rays in the atomic absorption spectrometer shown in FIG. 1.

FIG. 2 shows the path of rays in the atomic absorbtion spectrometer 11. The light source 10 consisting of a hollow cathode lamp directs the measuring light beam 14 via a fixed stationary concave mirror 32 and plane mirror 34 through a sample space 36 defined in a housing 38.

The burner 16 is movably mounted within the housing 38 for movement between a first sample measurement position and a second reference measurement position. The burner 16 is disposed in the sample space 36 below the measuring light beam 14 such that in the illustrated first position of the burner, the measuring light beam passes through the flame of the burner in which a cloud of atoms of the sample is formed. After having passed through the sample space 36, the measuring light beam is directed by a fixed stationary concave mirror 40 and plane mirror 42 to the inlet slit 44 of a monochromator 46. The monochromator 46 comprises a concave mirror 48 and a grating 50. Radiation diffracted by the grating 50 impinges through an outlet slit 52 of the monochromator 46 upon the detector 12.

The burner 16 is mounted for movement transverse to the optical axis of the measuring light beam 14 in the direction of the arrow 54 between the first position illustrated in solid lines and the second position illustrated in broken lines. In the second position, the burner 16 is disposed laterally of the measuring light beam 14. Thus, a single optical path is used for both sample and reference measurements.

Figure 3:
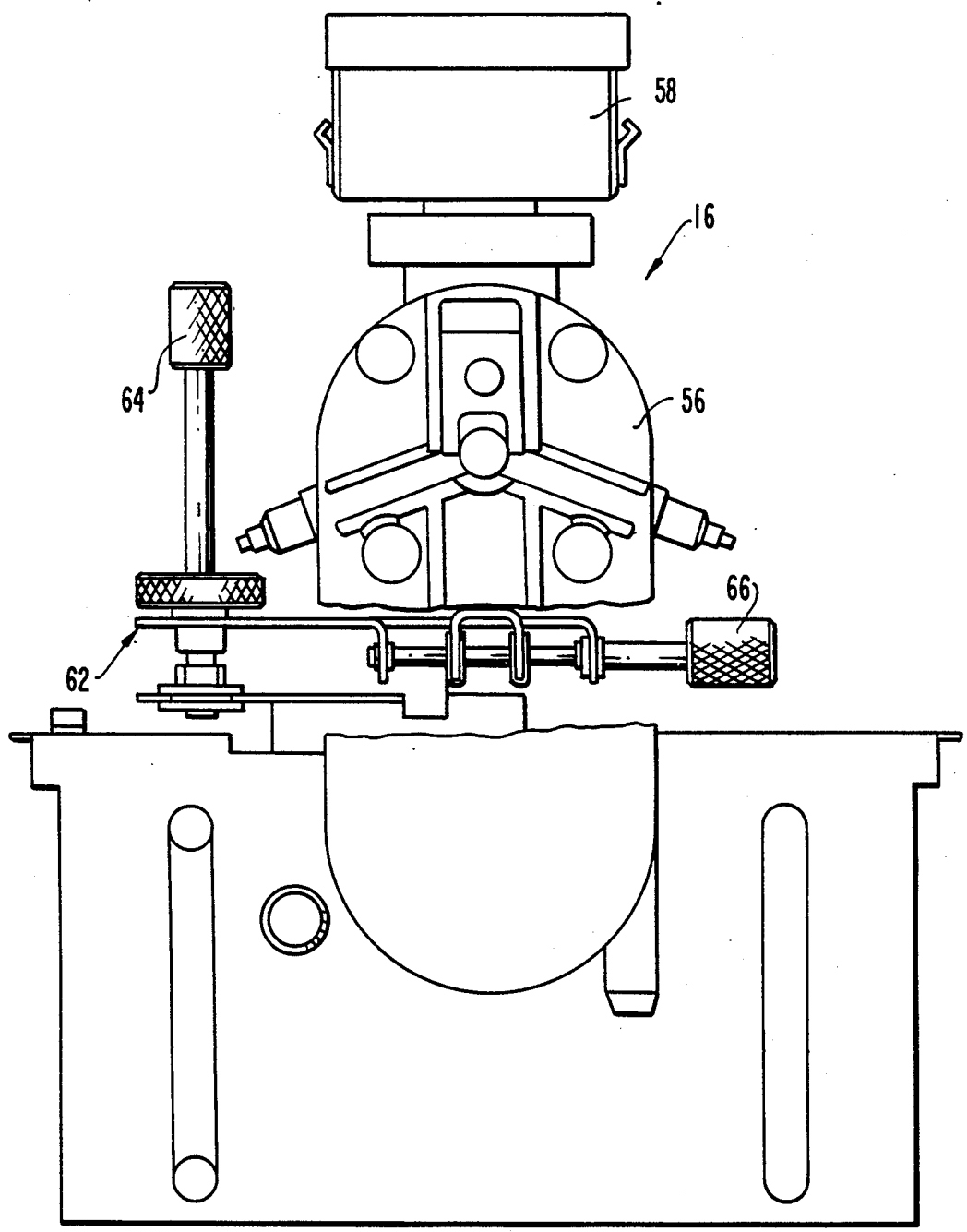
FIG. 3 is a side view of the movable burner of the present invention.
Figure 4:
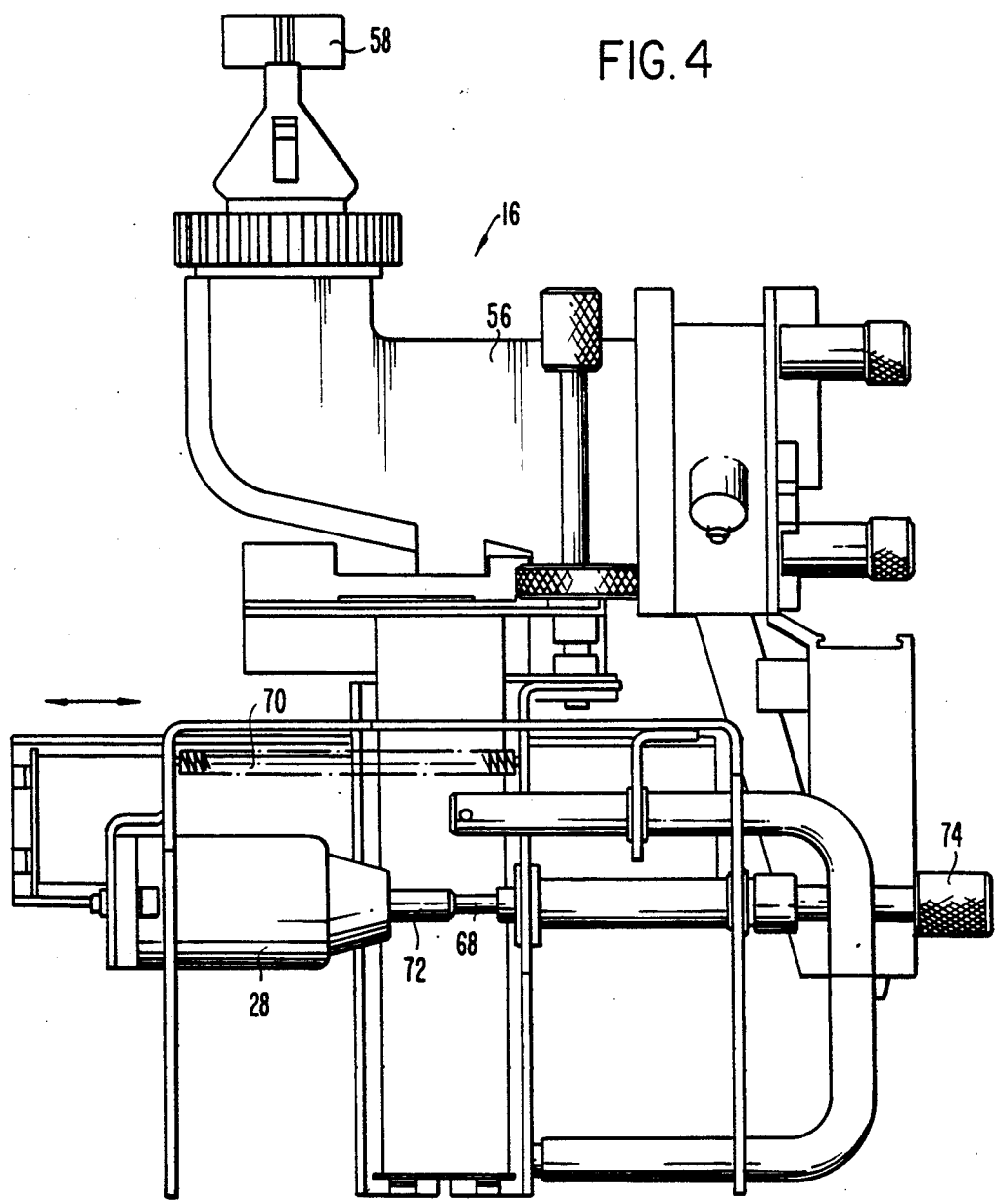
FIG. 4 is a view of the burner shown in FIG. 3, as viewed in the direction of the optical axis of the measuring light beam.

Referring to FIGS. 3 and 4, the burner 16 comprises a mixing chamber 56 and an oblong burner head 38. The measuring light beam 14 is guided in the longitudinal direction above the burner head 58 and thus extends horizontally in the plane of the paper of FIG. 3 above the burner head 58. The burner 16 is supported on a carriage 60 configured to be driven in a direction of movement 54 relative to the housing 38 between a first position and a second position. Adjusting mounting means 62 are provided for supporting the burner 16 on carriage 60 adjustably with respect to level and angle. The level adjustment is affected by means of an adjusting knob 64 and the angular adjustment is effected by means of an adjusting knob 66.

An adjustable stop or abutment 68 determines the first position of the carriage 60. The carriage 60 is biased in the direction towards the stop 68 by a helical return spring 70. The carriage 60 is selectively movable on a guide means against the action of the return spring 70 into the second position by the servomotor 28. The servomotor 28 is mounted on the carriage 60 and has a plunger 72 which extends and telescopes in the direction of movement of the carriage and engages the stop 68. The stop 68 is adjustable by an adjusting knob 74 and, in this way, the position of the burner in its first position can be accurately set and adjusted. The stop 68 is adjusted so that the burner flame is correctly aligned relative to the light beam 14 for a sample measurement upon movement of the burner 16 to the first position and engagement with the stop 68. Thus, as the burner is selectively moved back and forth during operation of the spectrometer, it will reproducibly assume in its first position a well-defined predetermined position relative to the measuring light beam 14.

The motor 28 is controlled by the microprocessor 22 such that the burner is driven out of the measuring light beam into the second position for a sample change. A reference measurement and drift compensation is made while the flame becomes stabilized outside the measuring light beam (i.e., while a cloud of atoms of new sample substantially constant throughout an extended period of time is formed in the flame) wherein the burner 16 is then returned to its first position for a sample measurement. Consequently, the measuring light beam is not interrupted during the sample measurement and therefore the total energy of the measuring light beam can be utilized for the measurement.

As can be seen, light source and detector variation compensation is attained in an atomic absorption spectrometer which utilizes fixed stationary optical elements to form a single optical light path for both sample and reference measurements. A desirable signal-to-noise ratio is attained without the necessity of movable optical elements and costly associated alignment tolerances.

As will be apparent to persons skilled in the art, various modifications and adaptations of the structure above described will become readily apparent without departure from the spirit and scope of the invention, the scope of which is defined in the appended claims.

What is claimed is:

1. An atomic absorption spectrometer comprising
a housing
a line emitting light source;
detector means for measuring the absorption of light from said light source,
an optical means for generating a measuring light beam along a fixed optical path from said light source to said detection means, said optical path extending though said housing,
atomizer means for atomizing a sample to generate a cloud of atoms for atomic absorption analysis with said light beam,
means for movably mounting said atomizer means within said housing for movement between a first sample measurement position wherein a cloud of atoms from said atomizer means is within said optical path and a second drift compensation reference measurement position wherein a cloud of atoms from said atomizer means is without said optical path,
signal processing means for processing signals from said detector means to provide an atomic absorption measurement and drift compensation, and
means controlling said signal processing means and said atomizer mounting means (i) to position said atomizer means in said first position for a first measuring time period to perform a sample measurement without interruption of the measuring light beam during said measuring time period, said measuring time period being sufficient for an entire atomic absorption measurement of an atomized sample and (ii) to position said atomizer means in said second position after said sample measurement for a second time period to provide drift compensation for said sample measurement.

2. The device of claim 1 wherein said atomizer means comprises an atomizer flame burner.

3. The device of claim 2 wherein said means for movably mounting said atomizer means comprises
a support carriage for mounting said burner and being movably mounted for movement between the first sample measurement position and the second reference measurement position, and
adjustable mounting means for mounting said burner on said carriage and being selectively adjustable with respect to angle and level.

4. The device of claim 3 comprising
a stop means for setting the position of said carriage in said first position,
a bias spring connected to said carriage for biasing said carriage toward said stop means, and
a servomotor means connected to said carriage for selectively moving said carriage toward said second position.

5. The device of claim 4 wherein said stop means includes means for adjusting the position of said stop means to vary the position of said burner in said measurement position.

6. The device of claim 4 wherein said servomotor is mounted on said carriage and has an extendable plunger element in engagement with said stop means and being extendable and retractable in the direction of travel of said carriage.

7. The device of claim 2 wherein said flame of said burner is within said optical path when said burner is in said sample measurement position and said flame is without said optical path with said burner being disposed transverse of said optical path when said burner is in said second reference measurement position.

8. The device of claim 1 wherein said optical means comprises a plurality of optically aligned optical elements with said elements being fixedly mounted in a stationary position.

9. The device of claim 1 wherein said controlling means comprises means for controlling a sample change in said atomizing means during said second time period and to reposition said atomizer means in said first position after said second time period.

10. The device of claim 9 wherein said second time period is sufficient for said atomizer means to stabilize after a sample change.

11. A method of light source-detector variation compensation in an atomic absorption spectrometric analysis of a sampling comprising:
directing a light beam for atomic absorption spectrometry along a predetermined, fixed optical path between a light emitting source and a detector means for performing sample and reference measurements,
positioning an atomizer means for atomizing a sample in a first predetermined position so that the atomized sample is in said optical path, performing a complete sample measurement with the total available energy of said light beam when the atomizer means is in said first position, positioning said atomizer means in a second predetermined position so that atomized sample from said atomizer means is without said optical path, performing a reference measurement when the atomizer means is in said second position, and compensating for light source variations in the sample measurement based upon the reference measurement.

12. The method of claim 11 wherein the step of directing a light beam comprises directing said light beam with stationary fixed optical elements along a single optical path for both sample and reference measurements.

13. The method of claim 11 wherein the atomizer means is an atomization burner and the step of positioning said burner in a first predetermined position comprises positioning said burner so that the flame is in said optical path and the step of positioning said burner in a second predetermined position comprises positioning said burner so that its flame is without said optical path.

14. The method of claim 11 wherein the atomizer means is an atomization burner movably mounted for movement between a first position whereby the burner flame is in the optical path and a second position whereby the flame is without the optical path comprising atomizing a first sample supplied to said burner, performing said sample measurement on the atomized first sample with the burner in said first position, positioning said burner in said second position, providing a second sample to said burner in said second position for burning, performing said reference measurement during stabilization of the burner flame for atomization of said second sample, and position said burner in said first position with atomization of said second sample in said optical path.

15. The method of claim 11 comprising positioning said atomizer means in said second predetermined position after the step of performing a sample measurement on a first sample atomized by said atomizer means, supplying a second sample to be analyzed while said atomizer means is in said second position, and performing said reference measurement while supplying said second sample to said atomizer means in said second position.

16. The method of claim 15 comprising atomizing said second sample while said atomizer means is in said second position and thereafter positioning said atomizer means in said first position for a sample measurement of said second sample.

17. The method of claim 11 which comprises changing the sample in said atomizer means while said atomizer means is in said second position and repositioning said atomizer means in said first position after the sample change.

18. The method of claim 17 which comprises maintaining said atomizer means in said second position until said atomizer means stabilizes after the sample change.

* * * * *